United States Patent
Iannotti et al.

(10) Patent No.: US 6,699,289 B2
(45) Date of Patent: Mar. 2, 2004

(54) AUGMENTED GLENOID COMPONENT HAVING AN INTERRUPTED SURFACE AND ASSOCIATED METHOD FOR SECURING THE AUGMENTED GLENOID COMPONENT TO A GLENOID SURFACE OF A SCAPULA

(75) Inventors: Joseph P. Iannotti, Bentleyville, OH (US); Gerald R. Williams, Jr., Villanova, PA (US)

(73) Assignee: DePuy Orthopaedics, Inc., Warsaw, IN (US)

( * ) Notice: Subject to any disclaimer, the term of this patent is extended or adjusted under 35 U.S.C. 154(b) by 0 days.

(21) Appl. No.: 10/036,583

(22) Filed: Dec. 31, 2001

(65) Prior Publication Data

US 2003/0125809 A1 Jul. 3, 2003

(51) Int. Cl.[7] .................................................. A61F 2/40
(52) U.S. Cl. ................................. 623/19.13; 623/19.11
(58) Field of Search ........................... 623/19.13, 19.11

(56) References Cited

U.S. PATENT DOCUMENTS 5,928,285 A * 7/1999 Bigliani et al. .......... 623/19.13
2001/0011192 A1 * 8/2001 Ondra et al. ............. 623/19.13

FOREIGN PATENT DOCUMENTS

FR        1064890 A1 *  6/2000   ............. A61F/2/40

OTHER PUBLICATIONS

Brochure for Total Shoulder COFIELD System., Smith & Nephew Richards, Inc.

* cited by examiner

Primary Examiner—Kevin Shaver
Assistant Examiner—Candice C. Melson
(74) Attorney, Agent, or Firm—Maginot, Moore & Beck (57) ABSTRACT

A glenoid component for securement to a glenoid surface of a scapula so as to provide a bearing surface for a head portion of a humerus includes a body having a first surface configured to contact the glenoid surface of the scapula and a second surface configured to receive the head portion of the humerus. The glenoid component also includes an interruption such as a buttress extending from the body. The interruption is configured to be received in a like-configured notch formed in the glenoid surface of the scapula. The interruption helps prevent movement of the glenoid component relative to the glenoid surface of the scapula after implant. The body also may include anchoring extending from the body for penetrating the glenoid surface of the scapula so as to help secure the body to the glenoid surface of the scapula. The glenoid component is used in one application to help correct bone defects and in another application for wear. A method of securing the glenoid component to a glenoid surface of a scapula so as to provide a bearing surface for a head portion of a humerus is also disclosed.

36 Claims, 11 Drawing Sheets

AUGMENTED GLENOID COMPONENT HAVING AN INTERRUPTED SURFACE AND ASSOCIATED METHOD FOR SECURING THE AUGMENTED GLENOID COMPONENT TO A GLENOID SURFACE OF A SCAPULA

TECHNICAL FIELD OF THE INVENTION

The present invention relates generally to a glenoid component, and more particularly to an augmented glenoid component and associated method for securing the augmented glenoid component to a glenoid surface of a scapula.

BACKGROUND OF THE INVENTION

During the lifetime of a patient, it may be necessary to perform a total shoulder replacement procedure on the patient as a result of, for example, disease or trauma. In a total shoulder replacement procedure, a humeral component having a head portion is utilized to replace the natural head portion of the arm bone or humerus. The humeral component typically has an elongated intramedullary stem which is utilized to secure the humeral component to the patient's humerus. In such a total shoulder replacement procedure, the natural glenoid surface of the scapula is resurfaced or otherwise replaced with a glenoid component that provides a bearing surface for the head portion of the humeral component.

As alluded to above, the need for a shoulder replacement procedure may be created by the presence of any one of a number of conditions. One such condition is the deterioration of the patient's scapula in the area proximate to the glenoid surface as a result of, for example, glenohumeral arthritis. In such a condition, the erosion of the patient's scapula is generally observed posteriorly on the glenoid surface. Such erosion of the scapula renders treatment difficult, if not impossible, with a conventional glenoid prosthesis.

Figure 1A:
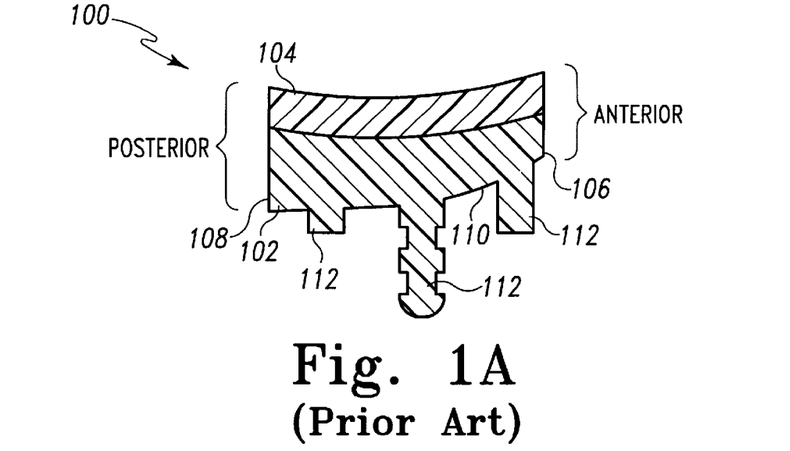
FIG. 1A is a side sectional view of a prior art augmented glenoid component.

In order to treat a condition in which a portion of the scapula has been eroded, a number of glenoid prostheses have heretofore been designed. Such glenoid prostheses, known generally as augmented glenoid prostheses, have a posterior edge that is thicker than the corresponding anterior edge. In FIG. 1A, a heretofore-designed augmented glenoid component 100 is shown. The glenoid component 100 has a metallic backing component 102 and plastic insert 104. The thickness of the metallic backing component 102 gradually increases from an anterior edge 106 to a posterior edge 108 thereof thereby creating a relatively smooth, arcuate-shaped medial surface 110 from which a number of posts or pegs 112 extend.

The design of the augmented glenoid component 100, however, has a number of associated drawbacks. For example, the relatively smooth, arcuate-shaped medial surface 110 may over time lead to loosening of the augmented glenoid component 100, thereby potentially necessitating additional surgical procedures to replace or reseat the component 100. Further, due to the configuration of the medial surface 110, a relatively high shear load is created along the implant-to-bone interface when the component 100 is implanted. The presence of a high shear load along the implant-to-bone interface tends to also cause loosening of the component 100 over a period of time. Post-operative loosening is the largest cause of failures of implanted glenoid components.

Figure 1B:
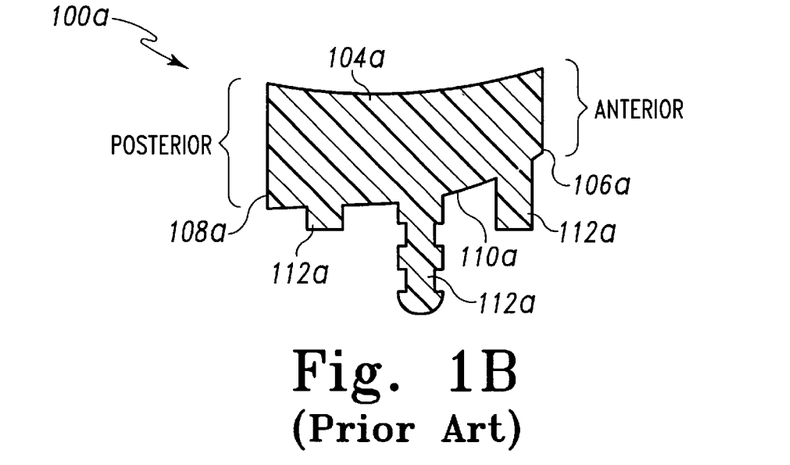
FIG. 1B is a side sectional view of another prior art augmented glenoid component.

In FIG. 1B another heretofore-designed augmented glenoid component 100a is shown. The glenoid component 100a has a single component plastic body 102a. The thickness of the plastic body 102a gradually increases from an anterior edge 106a to a posterior edge 108a thereof thereby creating a relatively smooth, arcuate-shaped medial surface 110a from which a number of posts or pegs 112a extend. The design of this augmented glenoid component 100a, however, suffers from at least the same drawbacks as the glenoid component 100.

Figure 1C:
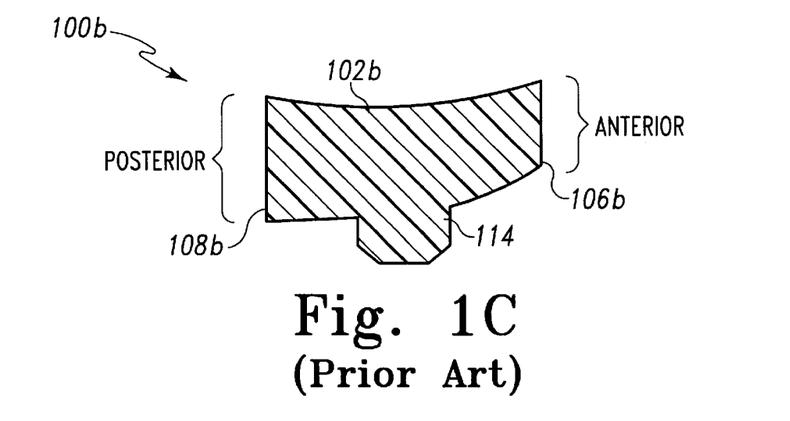
FIG. 1C is a side sectional view of another prior art augmented glenoid component.

In FIG. 1C another heretofore-designed augmented glenoid component 100b is shown. The glenoid component 100b also has a single component plastic body 102b. The thickness of the plastic body 102b gradually increases from an anterior edge 106b to a posterior edge 108b thereof thereby creating a relatively smooth medial surface 110b from which a keel 114 extends. The design of this augmented glenoid component 100b, however, suffers from at least the same drawbacks as the glenoid components 100 and 100a.

What is needed therefore is an augmented glenoid component that overcomes one or more of the above-mentioned drawbacks. What is further needed is an augmented glenoid component that is less susceptible to postoperative loosening relative to heretofore designed glenoid components.

SUMMARY OF THE INVENTION

The subject invention is a glenoid component and associated method for securement thereof to a glenoid surface of a scapula. Particularly, the subject invention is an augmented glenoid component and associated method for securement thereof to a glenoid surface of a scapula. More particularly, the subject invention is an augmented glenoid component having an interruption or the like and an associated method for securement of the augmented glenoid component to a glenoid surface of a scapula.

In one form, the interruption is defined by a buttress, step, shoulder, ledge, interface or the like that extends from a surface of a component body that defines at least a portion of the present augmented glenoid component. The body may also include anchoring. In one form, the anchoring of the body may comprise one or more anchors. An anchor may extend entirely from the surface of the body, entirely from the interruption, or from both the interruption and the surface (i.e. straddling).

In accordance with an embodiment of the subject invention, there is provided an augmented glenoid component for securement to a glenoid surface of a scapula so as to provide a bearing surface for a head portion of a humerus. The augmented glenoid component includes a body and a buttress. The body has a first body surface configured to contact the glenoid surface of the scapula, and a second body surface configured to be contacted by the head portion of the humerus. The buttress is formed in the first body surface of the body.

In accordance with another embodiment of the subject invention, there is provided an augmented glenoid component for securement to a glenoid surface of a scapula so as to provide a bearing surface for a head portion of a humerus. The augmented glenoid component includes a body, medial surface on the body, a humerus surface on the body, an interruption, and anchoring. The medial surface is configured to contact the glenoid surface of the scapula. The humerus surface is configured to be contacted by the head portion of the humerus. The interruption extends from the medial surface and defines a first interruption surface positioned relative to the medial surface at an angle θ in which $45° \leq \theta \leq 135°$, and a second interruption surface positioned relative to a line parallel to the first body surface an angle φ in which 0°≦φ≦90°.

In accordance with a further embodiment of the subject invention, there is provided a method of securing an augmented glenoid component to a glenoid surface of a scapula so as to provide a bearing surface for a head portion of a humerus. The augmented glenoid component has: (i) a body having: (a) a first body surface configured to contact the glenoid surface of the scapula, and (b) a second body surface configured to be contacted by the head portion of the humerus; and (ii) a buttress extending from the first body surface. The method includes the steps of (a) forming a buttress-shaped recess in the glenoid surface of the scapula; and (b) securing the augmented glenoid component to the glenoid surface of the scapula such that: (i) the first body surface is positioned in contact with the glenoid surface of the scapula, and (ii) the buttress is positioned in the step-shaped recess.

In all embodiments, the present augmented glenoid component provides good stabilization after implant. Further, the present augmented glenoid component converts normal high shear loads into compressive loading thereby reducing stress on the glenoid component. The present augmented glenoid component may be used to correct bone defects or wear.

It is therefore an object of the subject invention to provide a new and useful augmented glenoid component.

It is moreover an object of the subject invention to provide an improved augmented glenoid component.

It is a further object of the subject invention to provide a new and useful method of securing an augmented glenoid component to a glenoid surface of a scapula.

It is also an object of the subject invention to provide an improved method of securing an augmented glenoid component to a glenoid surface of a scapula.

It is yet another object of the subject invention to provide an augmented glenoid component and method of securing the same to a glenoid surface of a scapula that is less susceptible to post-operative loosening relative to heretofore designed glenoid components and methods of implanting the same.

The above and other objects, features, and advantages of the subject invention will become apparent from the following description and the attached drawings.

BRIEF DESCRIPTION OF THE DRAWINGS

Corresponding reference characters indicate corresponding parts throughout the several views. Like reference characters tend to indicate like parts throughout the several views.

DETAILED DESCRIPTION OF THE INVENTION

While the invention is susceptible to various modifications and alternative forms, specific embodiments thereof have been shown by way of example in the drawings and will herein by described in detail. It should be understood, however, that there is no intent to limit the invention to the particular forms disclosed, but on the contrary, the intention is to cover all modifications, equivalents, and alternatives falling within the spirit and scope of the invention as defined by the appended claims.

Figure 2:
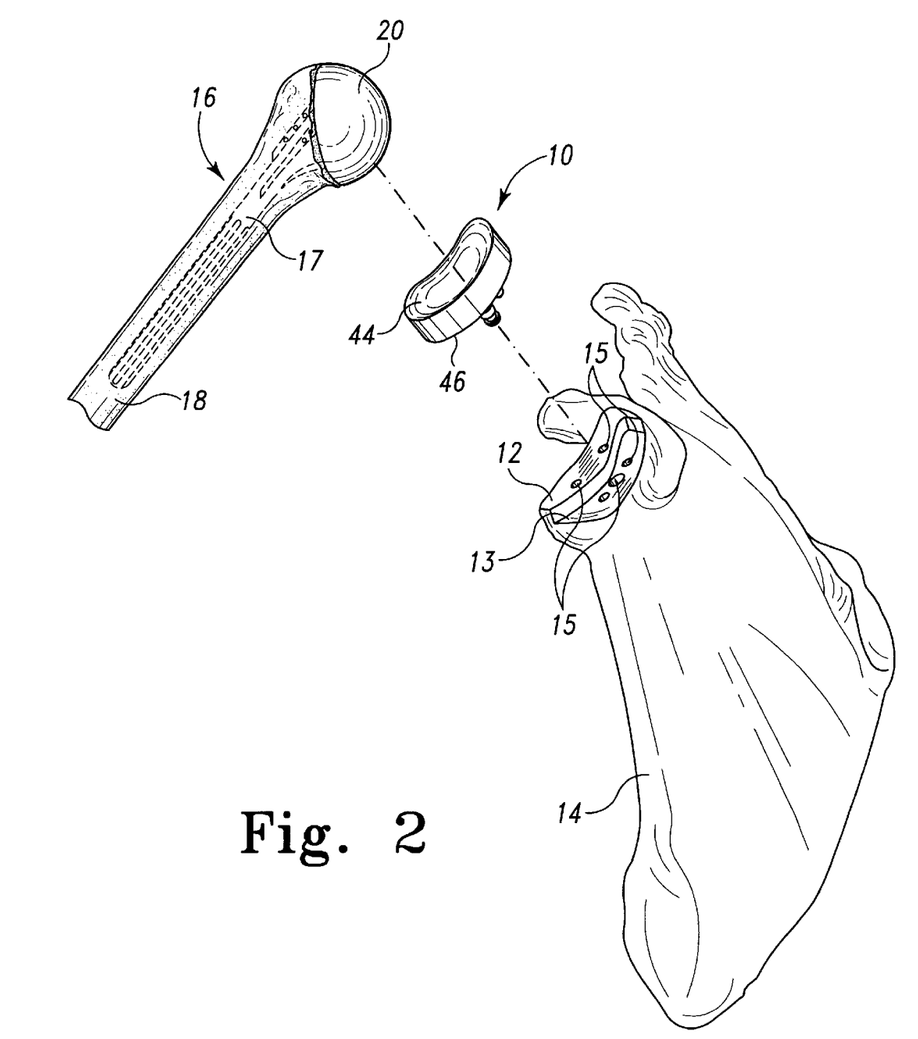
FIG. 2 is an exploded perspective view showing an augmented glenoid component that incorporates the features of the subject invention positioned between a prepared glenoid surface of a left scapula and a humeral component.
Figure 3:
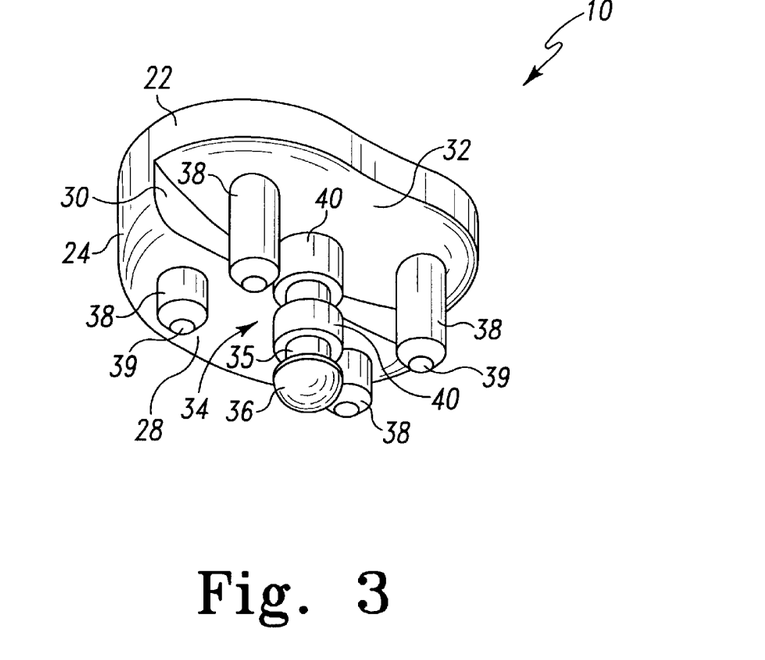
FIG. 3 is a bottom, right-angled perspective view of an embodiment of an augmented glenoid component in accordance with the present principles.
Figure 4:
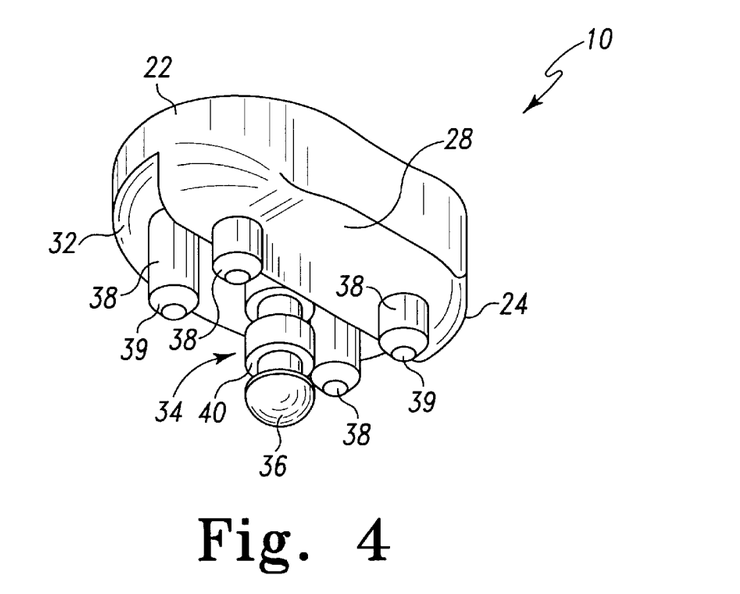
FIG. 4 is a bottom, left-angled perspective view of the augmented glenoid component of FIG. 3.

Referring now to FIG. 2, there is shown a general augmented glenoid component 10 in accordance with the present principles located between a glenoid surface 12 of a left scapula 14 and a humeral component 16. The augmented glenoid component 10 is representative of all embodiments of augmented glenoid components described herein. The humeral component 16 has been implanted or otherwise secured to a humerus 18. As shall be discussed below in greater detail, the glenoid component 10 is configured to be secured to the glenoid surface 12 of the scapula 14 with or without the use of bone cement in order to replace the natural glenoid surface 12 during a total shoulder replacement procedure. In such a manner, the augmented glenoid component 10 functions as a "replacement" bearing surface 44 for receiving a head portion (a prosthetic head portion) of the humerus 18 (as shown, a prosthetic head portion 20 attached to a stem 17 of the prosthetic humeral component 16 implanted in the humerus 18). A surface 46 of the augmented glenoid component contacts the glenoid surface 12.

In FIG. 2, the glenoid surface 12 has been prepared to receive the augmented glenoid component 10. Particularly, a notch 13 has been removed from the glenoid surface 12 to correspond in configuration to the augmented glenoid component 10. Additionally, a plurality of bores 15 have been prepared in the glenoid surface 12. The bores 15 are configured to receive anchors or anchoring of the augmented glenoid component 10 as discussed below.

Referring to FIGS. 3–7, there is shown an embodiment of the general glenoid component 10 shown in FIG. 2. The augmented glenoid component 10 includes a body 22 having a concave surface 26 on one end thereof. The concave surface 26 of the body 22 provides a smooth bearing surface for the head portion 20 of the humeral component 16 implanted into the humerus 18. As such, the concave surface 26 is configured with the same or greater curvature (with respect to the concavity thereof) as the curvature (with respect to the convexity thereof) of the head portion 20.

Figure 5:
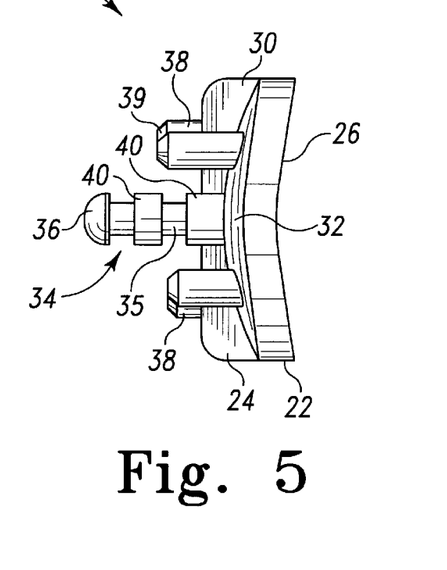
FIG. 5 is a front plan view of the augmented glenoid component of FIG. 3.
Figure 6:
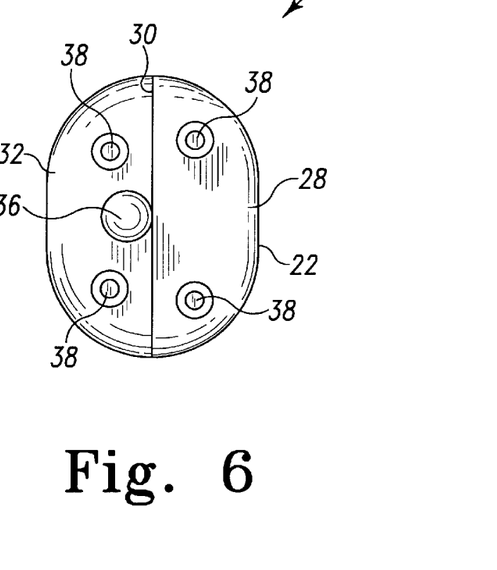
FIG. 6 is a bottom plan view of the augmented glenoid component of FIG. 3.
Figure 7:
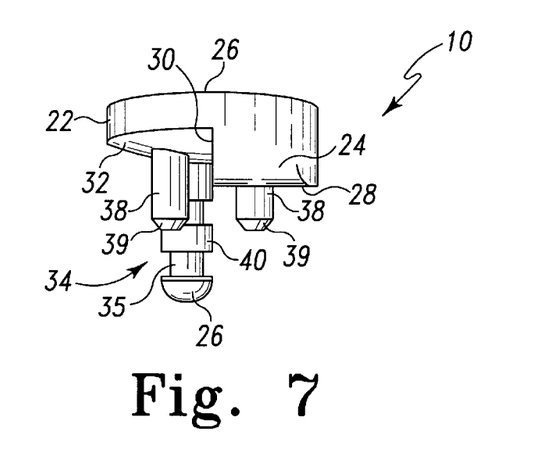
FIG. 7 is a side plan view of the augmented glenoid component of FIG. 3.

The body 22 includes an interruption in the form of a buttress, step, ledge or the like 24 on or from a body or medial surface 32 that defines a top surface 28 and a side surface 30. The top surface 28 is preferably substantially flat, but may be rounded or convex. The side surface 30 extends from the medial surface 32 to the top surface 28. The medial surface 32 is preferably rounded or convex as best seen in FIG. 5 but may be flat. The side surface 30 is shown substantially perpendicular to the top surface 28 and the medial surface 32. The side surface 30, however, may be angled relative to both surfaces 28 and 32 within an angle of 45° to 135°, inclusive.

The augmented glenoid component 10 also includes an anchor peg 34. The anchor peg 34 extends essentially perpendicular to the body surface 32. The anchor peg 34 includes a rounded head 36 that provides easier insertion into a hole or bore that has been drilled or otherwise formed in the glenoid surface 12 of the scapula 14. While not necessary, the glenoid component 10 is shown to include a plurality of stabilizing posts or pegs 38. Two pegs 38 are shown extending substantially perpendicular to the medial surface 32, while two pegs 38 are shown extending substantially perpendicular to the top surface 28. The length of the pegs 38 is preferably less than the length of the anchor peg 34. As well, the length of the pegs 38, regardless of position, are preferably essentially the same length relative to the replacement bearing surface 46, or of the ending length. The stabilizing pegs 38 are received into a number of respective stabilizing holes 15 (see FIG. 2) that are drilled or otherwise formed or prepared in the glenoid surface 12 of the scapula 14.

Although it is contemplated that the anchor peg 34 and/or any one or all of the stabilizing pegs 38 may be embodied as separate components that are secured to the body 22, the anchor peg 34 and any stabilizing pegs are preferably integrally formed with one another and the body 22. In one exemplary embodiment, the body 22, the anchor peg 34, and the stabilizing pegs 38 are integrally molded using a polymeric material such as polyethylene or ultra-high molecular weight polypropylene (UHMWPE). As well, the augmented glenoid component 10 may be formed of a plastic, a ceramic, or a composite material. Examples of these materials include a polyethylene, alumina, zirconia, and alumina/zirconia composite or composite material.

The buttress 24 extends a height or length relative to the body surface 32 that is preferably less than the length of the anchor peg 34. It should be appreciated that the length or height of the buttress may be longer or shorter depending on design choices as well as outer configuration and/or size.

The anchor peg 34 is herein shown in the figures to include two rings 40. However, it should be appreciated that the anchor peg 34 may be embodied to include any number of rings or no rings at all. For example, the anchor peg 34 may be embodied to include only a single (i.e. one) ring 40. In addition, although each of the rings 40 is herein shown in the figures to possess the same sized outer diameter, it should be appreciated that other ring or ring-like configurations such as fins (see FIG. 17) are also contemplated for use with the augmented glenoid component 10. For example, the rings 40 may be provided in a tapered configuration in which the respective outer diameters of the rings 40 gradually increases from the distal end of the anchor peg 34 to the proximal end portion of the anchor peg 34 (i.e. the ring positioned on the distal end of the anchor peg 34 has a smaller diameter relative to the ring positioned on the proximal end of the anchor peg 34). In such a configuration, an anchor hole drilled in the scapula 14 would be drilled in a similarly tapered manner so as to provide a corresponding sidewall configuration for engagement by the rings 40.

Although it is contemplated that the rings 40 may be embodied as separate components that are secured to the anchor peg 34, the rings 40 are preferably integrally formed with the anchor peg 34. Consistent with that described above, in one exemplary embodiment, the rings 40 are integrally molded with the anchor peg 34 (and hence also integrally molded with the body 22 and the stabilizing pegs 38 of the glenoid component 10a).

The rings 40 may be configured to slightly deform in a cementless application (or in oversize holes for cementless applications) when the anchor peg 34 is inserted into an anchor hole. This is caused when the rings 40 are advanced into the anchor hole since it is preferably drilled so as to have a diameter which is slightly larger than the diameter of a shaft portion 35 of the anchor peg 34, yet smaller than the outer diameter of the rings 40 thereby causing deformation of the rings 40 upon contact with the sidewalls of an anchor hole as the rings 40 are "forced" into the anchor hole. Such deformation of the rings 40 allows the rings 40 to secure the glenoid component 10a to the scapula 14 by providing resistance to removal or "pull out" of the anchor peg 34 from the anchor hole much in the same way that the threads of a screw provide resistance to pull out of the screw from the material into which it is driven. In addition, over a period of time subsequent to securement of the augmented glenoid component 10 to the scapula 14, bone tissue or other types of tissue will grow into the spaces between the rings 40 thereby providing further resistance to pull out of the anchor peg 34 from the anchor hole.

Such a configuration of the rings 40 and/or the buttress 24 as described above eliminates the need for the use of bone cement to secure the augmented glenoid component 10 to the glenoid surface 12 of the scapula 14 thereby reducing the complexity of a typical total shoulder replacement procedure along with eliminating any potential shortcomings associated with the use of bone cement. In particular, the above-described configuration of the buttress 24 provides a glenoid component 10 that "locks" into place upon insertion into the glenoid component 10 in the scapula 14. It is contemplated, however, that bone cement may be used if desired.

The stabilizing pegs 38 are not necessary but are preferably provided to help prevent rotation or other types of movement of the body 22 of the augmented glenoid component 10 in addition to the buttress 24 relative to the scapula 14 once the glenoid component 10 has been secured to the glenoid surface 12. The distal end of each of the stabilizing pegs 38 has a conical tip 39. The conical tip 39 functions as a "lead in" to facilitate insertion of the stabilizing pegs 38 into respective stabilizing holes drilled in the glenoid surface 12 of the scapula 14.

The stabilizing pegs 38 may be arranged in any orientation on the body 22 that fits the needs of an embodiment herein of an augmented glenoid component. In addition, it should be appreciated that any number of stabilizing pegs 38 may be utilized to fit the needs of a given augmented glenoid component. In particular, although the augmented glenoid component 10 is described herein as having four stabilizing pegs, and has significant advantages thereby in the present invention, it should be appreciated that the augmented glenoid component 10 may be alternatively embodied to include none or any number of stabilizing pegs 38.

Referring now to FIGS. 8–11 there is shown another embodiment of an augmented glenoid component that is generally designated 10a. The augmented glenoid component 10a includes a body 50 having a concave surface 52 on one end thereof. The concave surface 52 of the body 50 provides a smooth bearing surface for the head portion 20 of the humeral component 16 implanted into the humerus 18. As such, the concave surface 52 is configured with the same or greater curvature (with respect to the concavity thereof) as the curvature (with respect to the convexity thereof) of the head portion 20.

Figure 8:
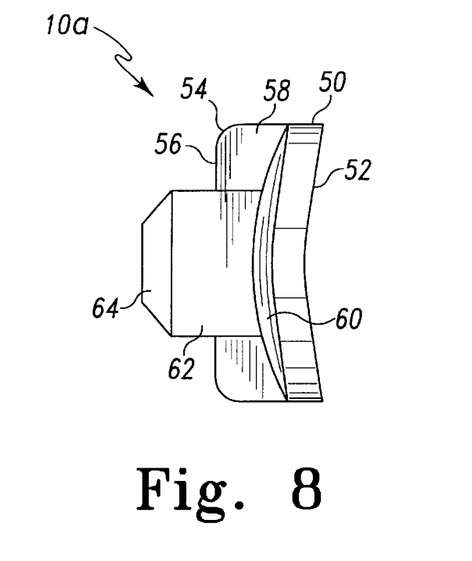
FIG. 8 is a front plan view of another embodiment of an augmented glenoid component in accordance with the present principles.
Figure 9:
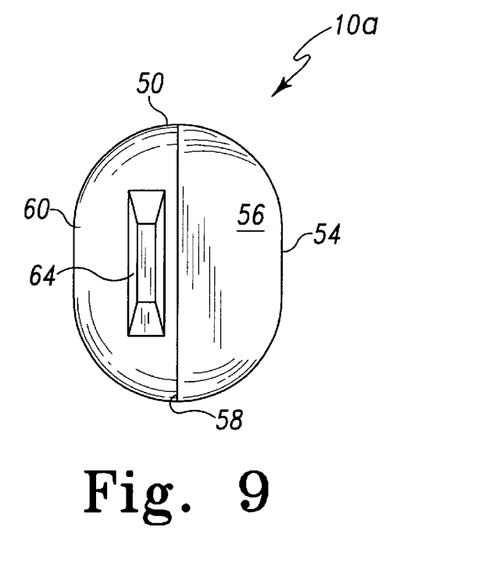
FIG. 9 is a bottom plan view of the augmented glenoid component of FIG. 8.
Figure 10:
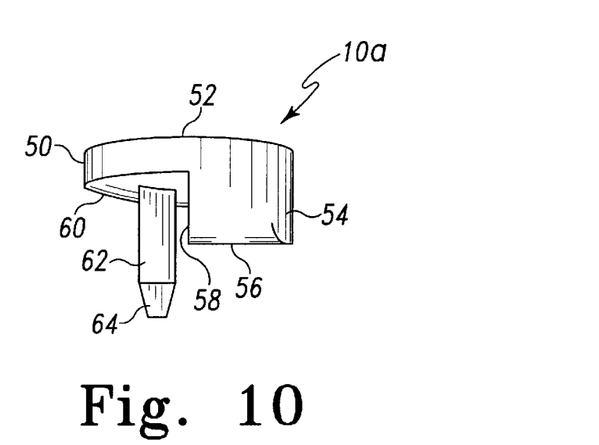
FIG. 10 is a side plan view of the augmented glenoid component of FIG. 8.
Figure 11:
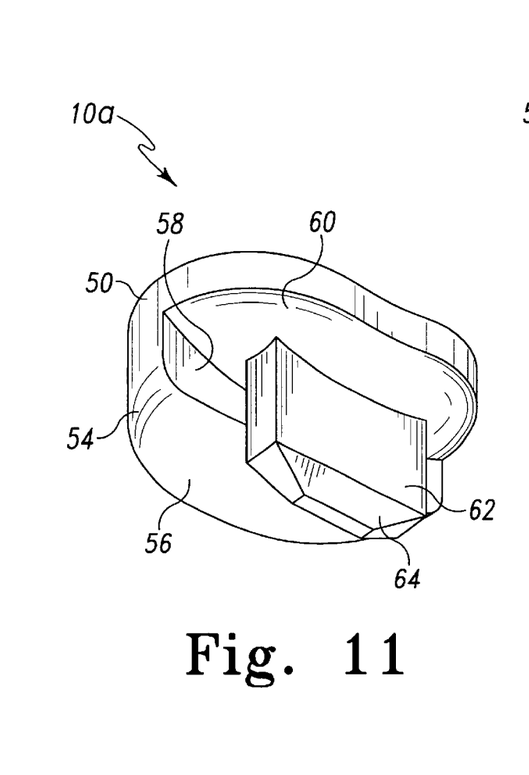
FIG. 11 is a bottom, right-angled perspective view of the augmented glenoid component of FIG. 8.
Figure 12:
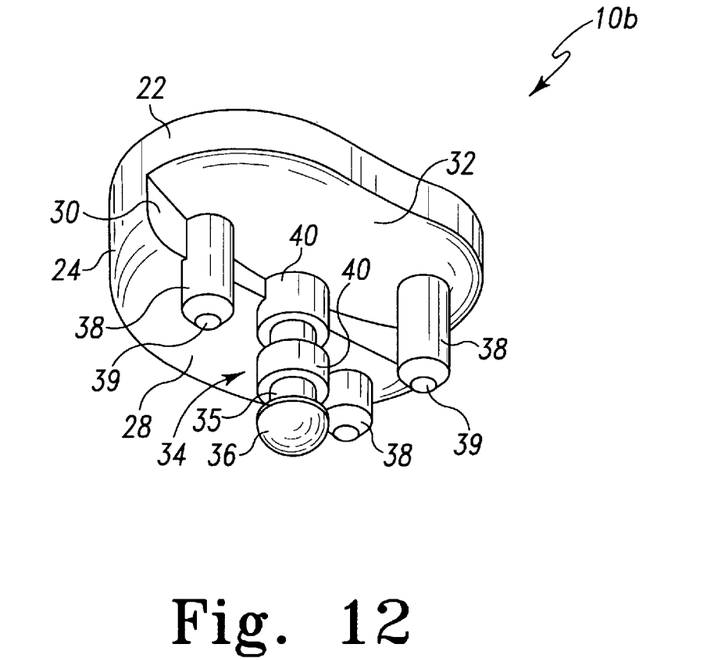
FIG. 12 is a bottom, right-angled perspective view of another embodiment of an augmented glenoid component in accordance with the present principles.
Figure 13:
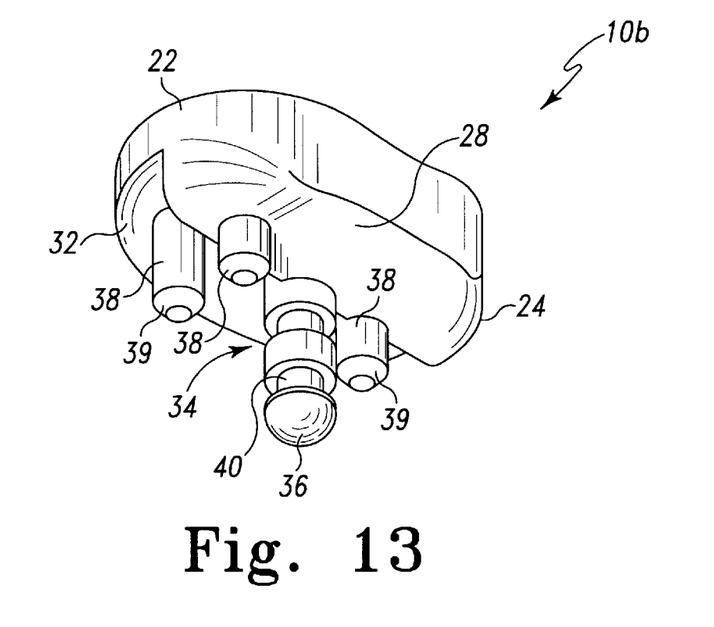
FIG. 13 is a bottom, right-angled rear perspective view of the augmented glenoid component of FIG. 12.
Figure 14:
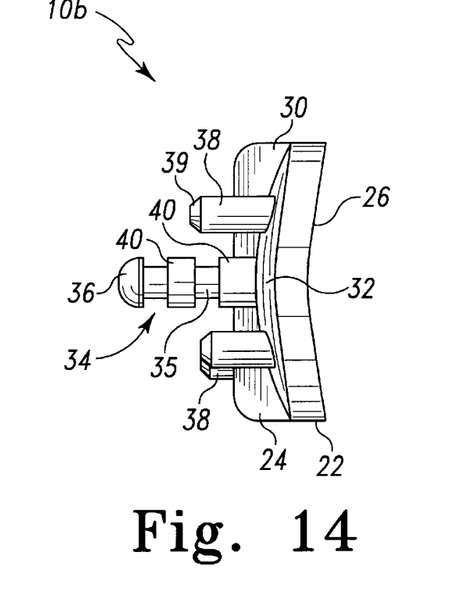
FIG. 14 is a side plan view of the augmented glenoid component of FIG. 12.
Figure 15:
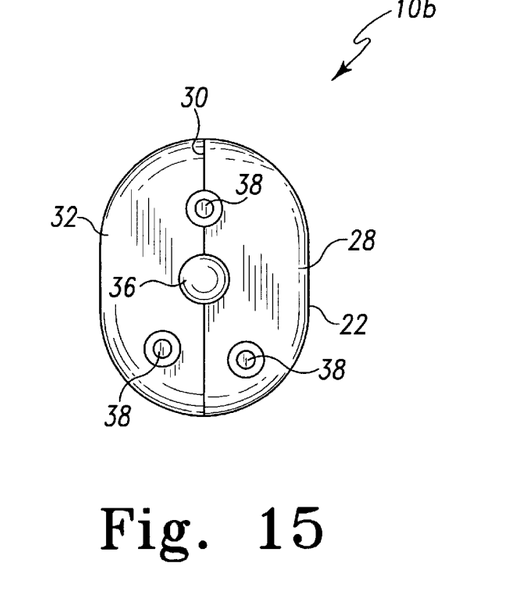
FIG. 15 is a bottom plan view of the augmented glenoid component of FIG. 12.
Figure 16:
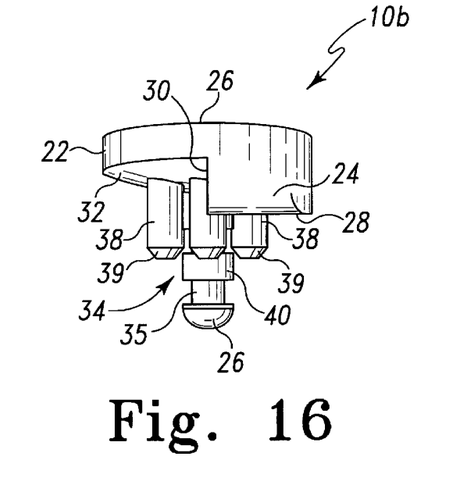
FIG. 16 is a side plan view of the augmented glenoid component of FIG. 12.

The body 50 includes an interruption in the form of a buttress, step, ledge or the like 54 on or from a medial or body surface 60 that defines a top surface 56 and a side surface 58. The top surface 56 is preferably substantially flat, but may be rounded or convex. The side surface 58 extends from the medial surface 60 to the top surface 56. The medial surface 60 is preferably rounded or convex as best seen in FIG. 8 but may be flat. The side surface 58 is shown substantially perpendicular to the top surface 56 and the medial surface 60. The side surface 58, however, may be angled relative to both surfaces 56 and 60 within an angle of 45° to 135°, inclusive.

The augmented glenoid component 10a also includes a keel 62. The keel 62 extends essentially perpendicular to the body surface 60. The keel 62 includes a tapered end 64 that provides easier insertion into a like-configured hole that has been drilled or otherwise formed or prepared in the glenoid surface 12 of the scapula 14.

Although it is contemplated that the keel 62 may be embodied as a separate component that is secured to the body 50, the keel 62 is preferably integrally formed with the body 50. In one exemplary embodiment, the body 50 and the keel 62 are integrally molded using a polymeric material such a polyethylene or an ultra-high molecular weight polypropylene (UHMWPE). As well, the glenoid component 10a may be formed of a plastic, a ceramic, or a composite material. Examples of these materials include a polyethylene, alumina, zirconia, and alumina/zirconia composite or composite material.

The buttress 54 extends a height or length relative to the medial surface 60 that is preferably less than the keel 62. It should be appreciated that the length or height of the buttress 54 may be longer or shorter depending on design choices. It should also be appreciated that the augmented glenoid component 10a does not show any stabilizing pegs. However, the augmented glenoid component 10a may include stabilizing pegs that may extend from the top surface 56 of the buttress 54.

Referring to FIGS. 12–16, there is depicted another embodiment of an augmented glenoid component, generally designated 10b. The augmented glenoid component 10b includes generally the same features and/or components as the augmented glenoid component 10 of FIGS. 3–7. In this embodiment, however, the anchor peg 34 extends from both the buttress 24 and the medial surface 32. Stated in another way, the anchor peg 34 straddles the buttress 24 and the medial surface 32. Additionally, the augmented glenoid component 10b has three (3) pegs 38. One of the pegs 38 extends from the medial surface 32. Another one of the pegs 38 extends from the buttress. Another one of the pegs 38 straddles the buttress 24 and the medial surface 32.

Figure 17:
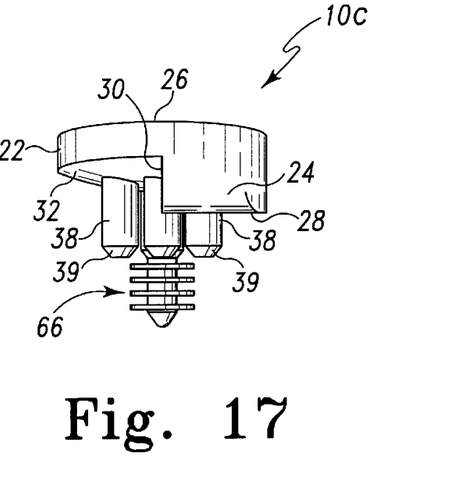
FIG. 17 is a side plan view of an other embodiment of an augmented glenoid component in accordance with the present principles.

FIG. 17 depicts yet another embodiment of an augmented glenoid component, generally designated 10c. The augmented glenoid component 10c is essentially the same as the augmented glenoid component 10b of FIGS. 12–16, with the exception of the anchor peg 34. The anchor peg 34 of the augmented glenoid component 10c includes a plurality of radial fins or the like 66. The fins 66 are deformable. This allows the anchor peg 34 to fit into an anchor bore in the glenoid surface 12 of the scapula 14, but aid in preventing the easy removal thereof.

Figure 18:
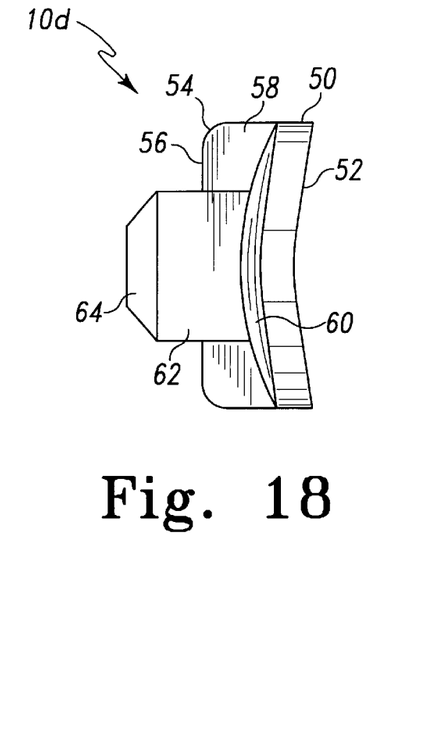
FIG. 18 is a side plan view of another embodiment of an augmented glenoid component in accordance with the present principles.
Figures 19, 20:
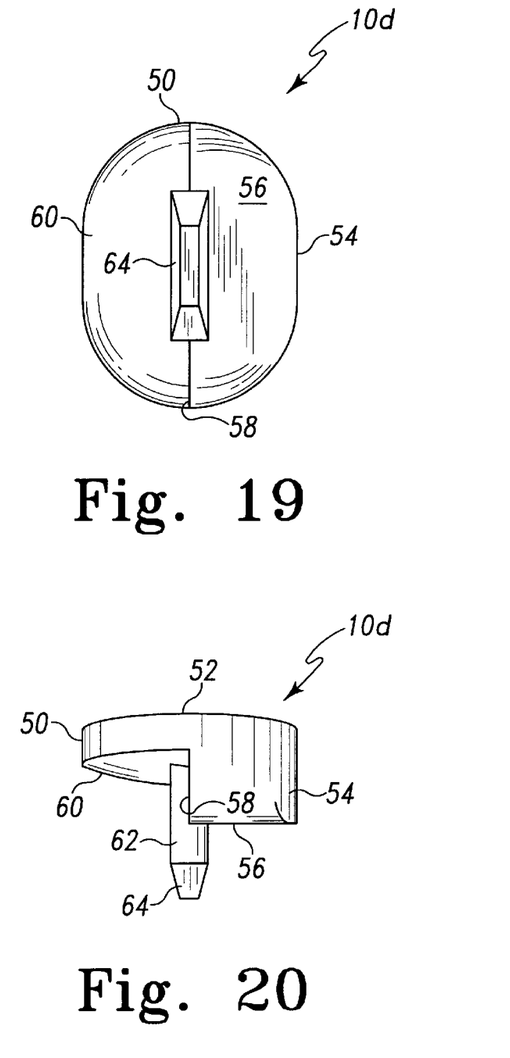
FIG. 19 is a bottom plan view of the augmented glenoid component of FIG. 18.
FIG. 20 is a side plan view of the augmented glenoid component of FIG. 18.
Figure 21:
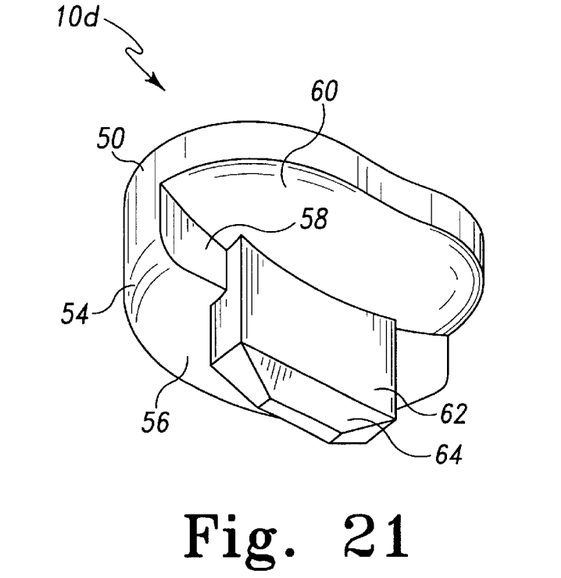
FIG. 21 is a bottom, right-angled perspective view of the augmented glenoid component of FIG. 18.

Referring to FIGS. 18–20, there is depicted another embodiment of an augmented glenoid component, generally designated 10d. The augmented glenoid component 10d is generally the same as the augmented glenoid component 10a of FIGS. 8–11. In this embodiment, however, the keel 62 straddles the buttress 54 and the medial surface 60. The keel 62 is thus essentially centered on the medial surface 60 of the body 52.

Referring now to FIGS. 22–25, there is depicted another embodiment of an augmented glenoid component generally designated 10e. The augmented glenoid component 10e is formed of two pieces or components, namely a backing member 70 and a backing member insert 72. The backing member 70 is adapted to be affixed or mounted to the glenoid surface 12 of the scapula 14, while the backing member insert 72 is adapted to be attached to the backing member 70.

The backing member 72 is preferably formed of a plastic, a ceramic, or a composite. Examples of these materials may be a polyethylene, alumina, zirconia, and alumina/zirconia composite or composite material. The backing member 70 is preferably formed of a metal, a ceramic, a composite, or a biological material. Examples of a biological material of the backing member 70 are bone, bone graft, or bone substitute material. Examples of a metal of the backing member 70 are titanium alloy, cobalt alloy, cobalt chromium, or stainless steel alloy. An example of ceramic of the backing member 70 includes alumina, zirconia or an alumina/zirconia composite ceramic. An example of the composite of the backing member 70 includes a carbon fiber/PEEK composite.

Figure 22:
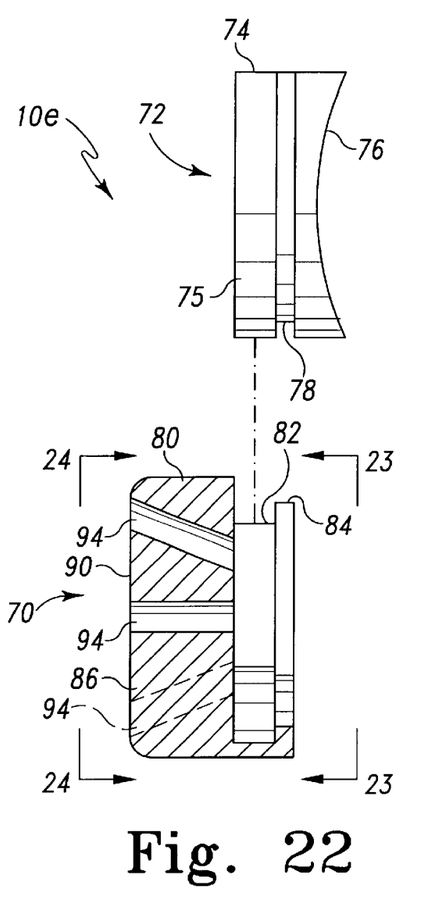
FIG. 22 is an exploded side view of a two-part embodiment of an augmented glenoid component in accordance with the present principles showing a backing member as one part thereof in cross-section.
Figure 23:
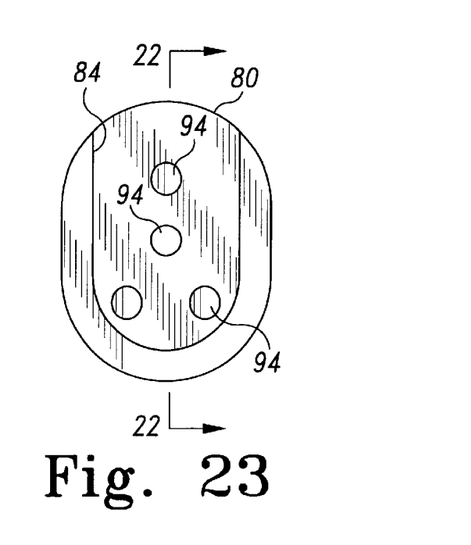
FIG. 23 is a bottom plan view of the backing member of FIG. 22 taken along line 23—23 thereof, as viewed in the direction of the arrows.
Figure 24:
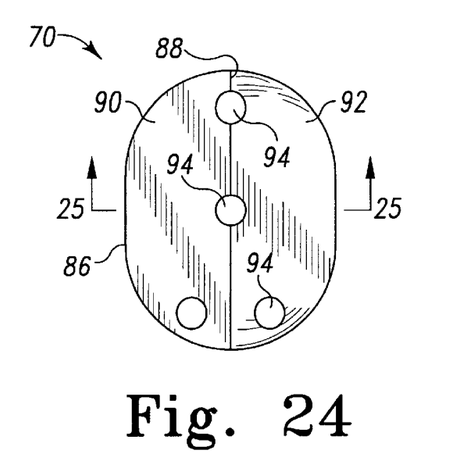
FIG. 24 is a top plan view of the backing member of FIG. 22 taken along line 24—24 thereof, as viewed in the direction of the arrows.

The backing member insert 70 includes a body 74 having a concave surface 76 on one end thereof. The concave surface 76 of the body 70 provides a smooth bearing surface for the head portion 20 of the humeral component 16 implanted into the humerus 18. As such, the concave surface 76 is configured with the same or greater curvature (with respect to the concavity thereof) as the curvature (with respect to the convexity thereof) of the head portion 20. The backing member insert 72 also includes a peripheral slot 78 that is adapted to allow the backing member insert 72 to be received and held by the backing member 70 in a manner as described below.

Figure 25:
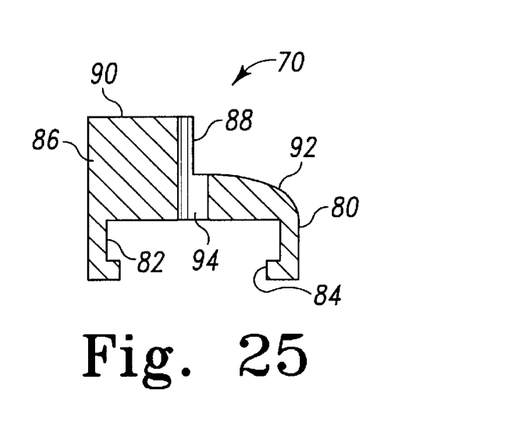
FIG. 25 is a cross-sectional view of the backing member of FIG. 24 taken along line 25—25 thereof, as viewed in the direction of the arrows.

The backing member 70 has a body 80 having an interruption formed as a buttress, step, ledge or the like 86 that defines a top surface 90 and a side surface 88. The top surface 90 is preferably substantially flat, but may be rounded or convex. The side surface 88 extends from a body surface 92 to the top surface 90. The body surface 92 is preferably rounded or convex as best seen in FIG. 25. The side surface 88 is shown substantially perpendicular to the top surface 90 and the body surface 92. The side surface 88, however, may be angled relative to both surfaces 90 and 92 within an angle of 45° to 135°, inclusive.

As best seen in FIG. 25, the backing member 70 includes a horseshoe-shaped rim 84 that defines a horseshoe-shaped slot 82. The rim 84 and slot 82 cooperate/are adapted to slidingly receive the backing member insert 72. In particular, a portion 75 of the backing member insert 72 is received in the slot 82 while the rim 84 engages the slot 78 of the backing member 72. It should be appreciated that the backing member 70 is first affixed to the scapula 14 before the backing member insert 72 is attached thereto. As explained in greater detail below, the backing member 70 is affixed to the scapula 14 via fasteners. Of course, other types of connectors may be used for the backing member 70 and the backing member insert 72.

The backing member 70 also includes a plurality of bores 94 each of which is adapted to allow a screw, nail, or other fastener to extend therethrough. In this manner, the backing member 70 is secured to the glenoid area 12 of the scapula 14. The backing member 70 is shown with three bores 94 through the buttress 86, and three bores 94 through the body surface 92. It should be appreciated that the backing member 70 may contain more or less bores, in various places. Preferably, the middle two bores are substantially perpendicular to the buttress top surface 90, while the outer bores are angled outwardly. Such configuration provides a secure attachment of the backing member 70 to the glenoid surface 12 of the scapula 14.

Figure 26:
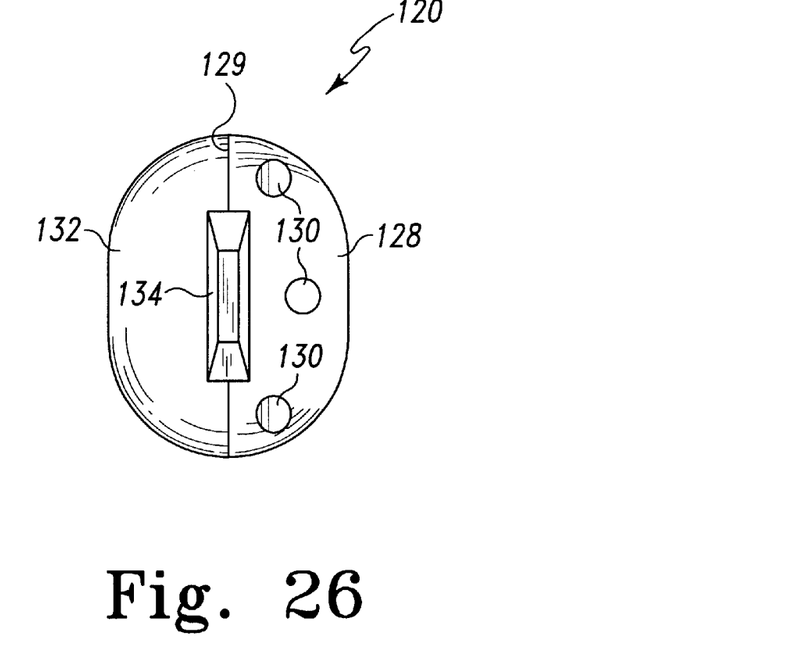
FIG. 26 is a bottom plan view of another embodiment of an augmented glenoid component in accordance with the present principles.

Referring to FIG. 26, there is shown another embodiment of a backing member, generally designated 120, in like kind to the backing member 70 of FIGS. 22–25. The backing member 120 includes a body 122 having a horseshoe-shaped slot 124 surrounded by a horseshoe-shaped rim 126. The slot 124 and rim 126 are configured to receive a backing member insert (not shown) in like kind to the backing member insert 72 of FIG. 22.

In accordance with an aspect of the present invention, the backing member 120 has a buttress 128 that covers approximately one-half of the body 122 or of a medial surface 132. The buttress 128 defines a side surface 129 that is preferably essentially perpendicular to a preferably, but not necessarily, convex or rounded medial surface 132. The side surface 129, however, may be within an angle of 45° to 135°, inclusive (i.e. the side surface defines an angle θ, wherein 45°≦θ≦135°, with respect to the medial surface 132). The buttress 128 also includes a plurality of bores 130. The bores 130 are configured to allow fasteners to extend therethrough and capture the ends thereof in order to affix the body 122 onto the glenoid surface 12 of the scapula 14. The backing member 120 further includes a keel 134 in like kind to the keel 62 of FIGS. 8–11 and FIGS. 18–21. The keel 134 extends substantially perpendicular from the medial surface 132 and the buttress 128 in a straddling manner.

Figure 27:
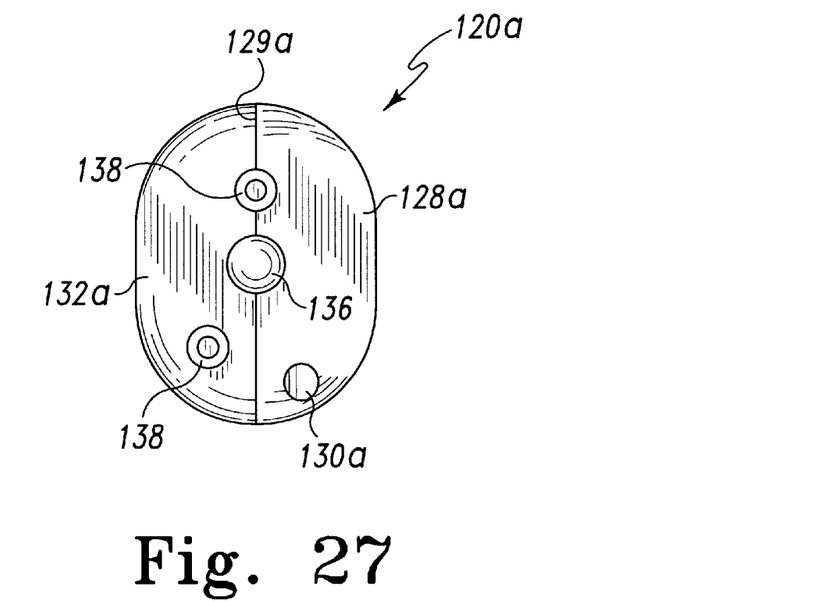
FIG. 27 is a bottom plan view of another embodiment of an augmented glenoid component in accordance with the present principles.

FIG. 27 provides another alternative embodiment of the backing member 120. In particular, the backing member 120a of FIG. 27 includes many of the same features as the backing member 120 with the exception of the keel 134. Rather than a keel, the backing member 120a includes an anchor peg or post 136 in like kind to the post 34 of FIGS. 3–7. The anchor peg 136 is preferably configured in the same manner as the anchor peg 34 and extends substantially perpendicular to the medial surface 132a and the buttress 128a in a straddling manner. In addition, the backing member 120a includes a pair of stabilizing posts or pegs 138 in like kind to the stabilizing posts 38 of FIGS. 3–7. In the present case, however, one stabilizing post 38 extends outwardly from the medial surface 132a, while another stabilizing post 38 straddles the buttress 128a and the medial surface 132a. The backing member 120a further includes a bore 130a extending through the buttress 128a.

USE OF THE PRESENT INVENTION

Figure 28:
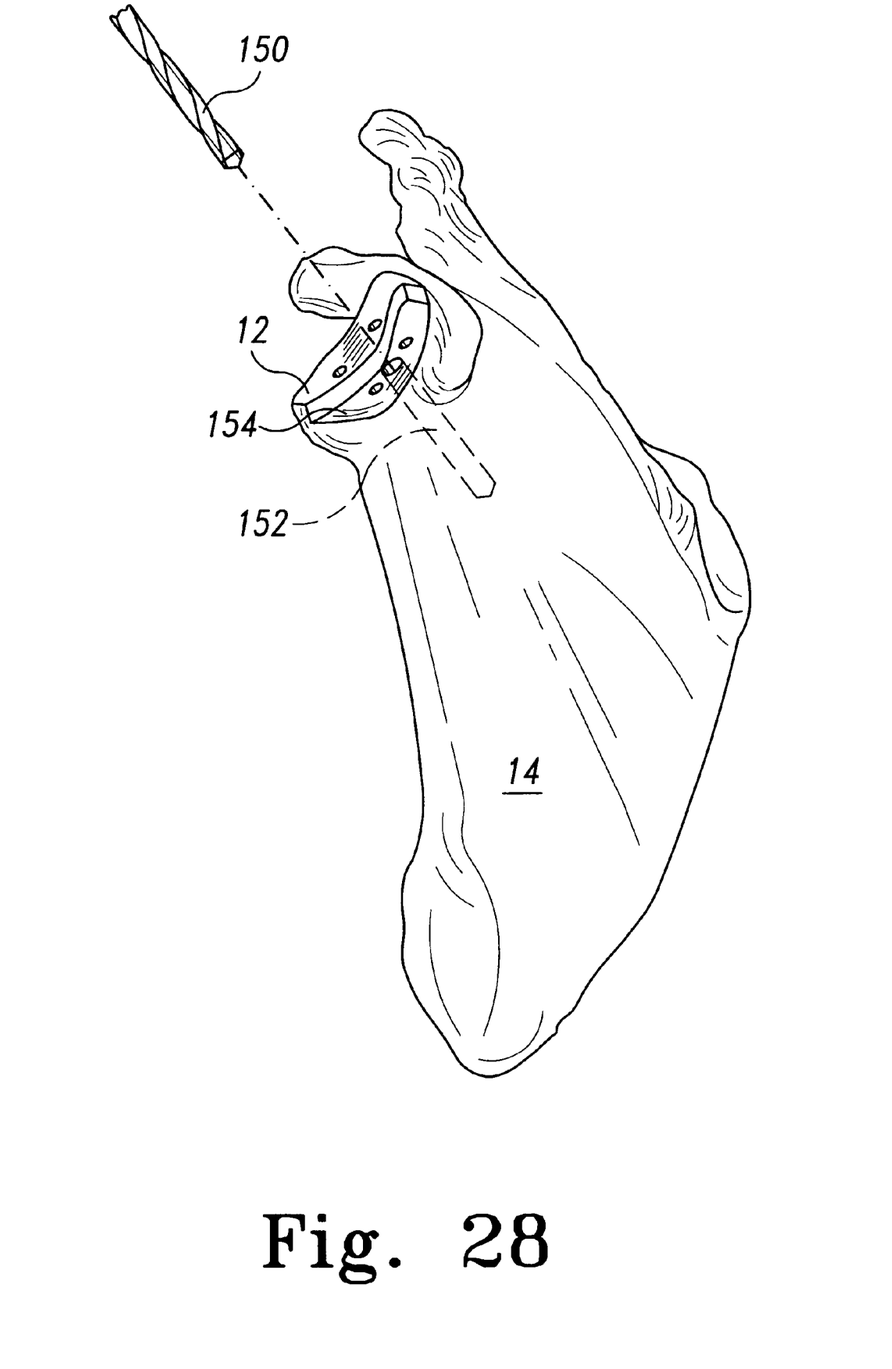
FIG. 28 is a perspective view of a scapula having been prepared for securement of an augmented glenoid component in accordance with the present principles.

The augmented glenoid component 10 of the present invention is utilized in the performance of a total shoulder replacement procedure in order to provide an artificial bearing surface for the head portion of the humerus with or without the use of bone cement. Referring to FIG. 28, there is depicted a left scapula 14 in which an augmented glenoid component 10 will be affixed.

In particular, an anchor hole 152 and stabilizing holes are drilled or otherwise formed in the glenoid surface 12 of the scapula 14 by use of a suitable drilling tool (as represented by the drill bit 150). For those augmented glenoid components having a keel or other type or style of main anchor or stabilizer, a complementary recess is formed in the glenoid surface 12. It should be appreciated that a drill guide or pattern (not shown) may be utilized to properly position and align the holes on the glenoid surface of the scapula 14. Further, the anchor hole 152 is drilled to accommodate the anchor peg of the glenoid component, or a keel (in which case the "hole" is shaped to accept the configuration of the keel). Alternatively, various holes may be formed in the scapula 14 to accommodate fasteners rather than pegs, when utilizing a two-part glenoid component having a backing member.

In addition to any holes to accommodate pegs and/or a keel, a notch 154 is formed to accommodate the buttress of the glenoid component. This may be accomplished utilizing an appropriate saw, reamer, router or the like. Typically, the notch 154 is formed at a posterior location of the glenoid surface 12 of the scapula 14.

Once any holes and the notch 154 have been formed in the glenoid surface 12 of the scapula 14, the glenoid component 10 is secured to the scapula 14. In particular, the glenoid component 10 is oriented such that the buttress is received in the notch 154 and any anchor peg, keel, and/or stabilizing pegs are received in the respective holes (or in the case of fasteners, that the holes in the backing member are oriented over the holes in the scapula). Thereafter, the glenoid component 10 is advanced toward the glenoid surface 12.

Hence, insertion of the buttress into the notch 154 retains the body of the glenoid component 10 into contact with the glenoid surface 12 of the scapula 14. Moreover, insertion of the anchor peg, keel and/or stabilizing pegs into corresponding holes in the manner described above prevents rotation or other types of movement of the body of the glenoid component 10 relative to the glenoid surface 12 of the scapula 14.

Once the glenoid component 10 has been secured to the glenoid surface 12 of the scapula 14 in the manner described, the concave surface 26 of the body 22 of the glenoid component 10 provides a bearing surface for receiving the head portion 20 of the humeral component 16 implanted in the humerus 18. In such a manner, the concave surface 26 of the body portion 22 functions as a suitable artificial replacement for the natural glenoid surface 12 of the scapula 14.

While the invention has been illustrated and described in detail in the drawings and foregoing description, such an illustration and description is to be considered as exemplary and not restrictive in character, it being understood that only the preferred embodiment has been shown and described and that all changes and modifications that come within the spirit of the invention are desired to be protected.

There are a plurality of advantages of the present invention arising from the various features of the glenoid component described herein. It will be noted that alternative embodiments of the glenoid component of the present invention may not include all of the features described yet still benefit from at least some of the advantages of such features. Those of ordinary skill in the art may readily devise their own implementations of a glenoid component that incorporate one or more of the features of the present invention and fall within the sprit and scope of the present invention as defined by the appended claims.

For example, the embodiment of one bearing component in accordance with the concepts of the present invention has herein been described in regard to the glenoid component 10. However, it should be appreciated that the concepts of the present invention may also be incorporated into an acetabular, patellar, femoral, humeral, tibial, ulnar, radial, wrist, and/or ankle component for a prosthetic joint assembly.

What is claimed is:

1. An augmented glenoid component for securement to a glenoid surface of a scapula so as to provide a bearing surface for a head portion of a humerus, the augmented glenoid component comprising:
    a body;
    a first surface on said body and configured to contact the glenoid surface of the scapula;
    a second surface on said body and configured to be contacted by the head portion of the humerus; and
    a buttress formed in said first surface of said body,
    wherein said body further includes anchoring adapted to penetrate the glenoid surface of the scapula, and
    wherein said anchoring extends entirely from said buttress.

2. The augmented glenoid component of claim 1, wherein:
    said buttress defines a first buttress surface and a second buttress surface; and
    said first buttress surface is positioned relative to said first surface at an angle $\theta$, wherein $45°<\theta<135°$.

3. The augmented glenoid component of claim 2, wherein said anchoring is substantially perpendicular to said second buttress surface.

4. The augmented glenoid component of claim 2, wherein said anchoring is substantially parallel to said first buttress surface.

5. The augmented glenoid component of claim 2, wherein said second buttress surface is positioned perpendicular to said first buttress surface.

6. The augmented glenoid component of claim 5, wherein said second buttress surface is substantially parallel to said first body surface.

7. An augmented glenoid component for securement to a glenoid surface of a scapula so as to provide a bearing surface for a head portion of a humerus, the augmented glenoid component comprising:
    a body;
    a first surface on said body and configured to contact the glenoid surface of the scapula;
    a second surface on said body and configured to be contacted by the head portion of the humerus; and
    a buttress formed in said first surface of said body,
    wherein said body further includes anchoring adapted to penetrate the glenoid surface of the scapula, and
    wherein said anchoring extends from said first surface and said buttress.

8. The augmented glenoid component of claim 7, wherein said anchoring comprises an anchor peg.

9. The augmented glenoid component of claim 7, wherein said anchoring comprises an anchor keel.

10. The augmented glenoid component of claim 7, wherein said anchoring straddles said first surface and said buttress.

11. An augmented glenoid component for securement to a glenoid surface of a scapula so as to provide a bearing surface for a head portion of a humerus, the augmented glenoid component comprising:
    a body;
    a first surface on said body and configured to contact the glenoid surface of the scapula;
    a second surface on said body and configured to be contacted by the head portion of the humerus; and
    a buttress formed in said first surface of said body,
    wherein said body comprises a backing member having said first surface of said body, said second body surface of said body, and said buttress defined therein, and the augmented glenoid component further comprises: a bearing insert member securable to said backing member,
    wherein said backing member is formed of one of a metal, a ceramic, a composite, and a biological material,
    wherein said bearing insert member is formed of one of a plastic, a ceramic, and a composite,
    wherein said backing member includes a plurality of holes each of which is configured to allow passage of a securing member for securing said backing member to the glenoid surface of the scapula, wherein said plurality of holes extend outwardly from said buttress member.

12. The augmented glenoid component of claim 11, wherein said biological material of said backing member comprises one of bone, bone graft, and bone substitute material.

13. The augmented glenoid component of claim 11, wherein said metal of said backing member comprises one of a titanium alloy, a cobalt alloy, and a stainless steel alloy.

14. The augmented glenoid component of claim 11, wherein said ceramic of said backing member comprises an alumina, a zirconia, and an alumina/zirconia composite ceramic.

15. The augmented glenoid component of claim 11, wherein said composite of said backing member comprises a carbon fiber/PEEK composite.

16. The augmented glenoid component of claim 11, wherein said bearing insert member comprises one of a polyethylene, alumina, zirconia, and alumina/zirconia composite or composite material.

17. An augmented glenoid component for securement to a glenoid surface of a scapula so as to provide a bearing surface for a head portion of a humerus, the augmented glenoid component comprising:

a body having a medial surface and a humerus surface;

said medial surface configured to contact the glenoid surface of the scapula;

said humerus surface configured to be contacted by the head portion of the humerus;

an interruption extending from said medial surface and defining a first interruption surface positioned relative to said medial surface at an angle $\theta$ in which $45°<\theta<135°$, and a second interruption surface positioned relative to a line parallel to said medial surface at an angle $\Phi$ in which $0°<\Phi<90°$; and anchoring, Wherein said anchoring extends from said medial surface, and wherein said anchoring extends from said medial surface and said interruption.

18. The augmented glenoid component of claim 17, wherein said anchoring comprises a plurality of anchor pegs.

19. The augmented glenoid component of claim 17, wherein said anchoring comprises a keel.

20. The augmented glenoid component of claim 17, wherein said anchoring straddles said interruption and said medial surface.

21. An augmented glenoid component for securement to a glenoid surface of a scapula so as to provide a bearing surface for a head portion of a humerus, the augmented glenoid component comprising:

a body having a medial surface and a humerus surface;

said medial surface configured to contact the glenoid surface of the scapula;

an interruption extending from said medial surface and defining a first interruption surface positioned relative to said medial surface at an angle $\theta$ in which $45°<\theta<135°$, and a second interruption surface positioned relative to a line parallel to said medial surface at an angle $\Phi$ in which $0°<\Phi<90°$; and anchoring, wherein said body comprises a backing member having said medial surface, said humerus body surface, and said interruption defined therein; and the augmented glenoid component further comprises: a bearing insert member securable to said backing member, and wherein (i) said backing member is formed of one of a metal, a ceramic, a composite, and a biological material; and (ii) said bearing insert member is formed of one of a plastic, a ceramic, and a composite.

22. The augmented glenoid component of claim 21, wherein said biological material of said backing member comprises one of bone, bone graft, and bone substitute material.

23. The augmented glenoid component of claim 21, wherein said metal of said backing member comprises one of a titanium alloy, a cobalt alloy, and a stainless steel alloy.

24. The augmented glenoid component of claim 21, wherein said ceramic of said backing member comprises an alumina, a zirconia, and an alumina/zirconia composite ceramic.

25. The augmented glenoid component of claim 21, wherein said composite of said backing member comprises a carbon fiber/PEEK composite.

26. The augmented glenoid component of claim 21, wherein said bearing insert member comprises one of a polyethylene, alumina, zirconia, and alumina/zirconia composite or composite material.

27. The augmented glenoid component of claim 21, wherein said backing ember includes a plurality of holes each of which is configured to allow passage of a securing member for securing said backing member to the glenoid surface of the scapula.

28. A method of securing an augmented glenoid component to a glenoid surface of a scapula so as to provide a bearing surface for a head portion of a humerus, said augmented glenoid component having (i) a body having (a) a first body surface configured to contact the glenoid surface of the scapula, and (b) a second body surface configured to be contacted by the head portion of the humerus, and (ii) a buttress extending from said first body surface, the method comprising the steps of:

forming a buttress-shaped recess in a glenoid surface of a scapula; and securing said augmented glenoid component to the glenoid surface of the scapula such that (i) said first body surface is positioned in contact with the glenoid surface of the scapula, and (ii) said buttress is positioned in said step-shaped recess, wherein said forming step includes the step of removing said buttress-shaped recess in the glenoid surface of the scapula with a bone cutter.

29. The method claim 28, wherein said removing step includes forming at least a portion of said buttress-shaped recess with a concave surface.

30. The method of claim 28, wherein:

said augmented glenoid component further has (i) a backing member, and (ii) a bearing insert member which is securable to said backing member;

said first body surface of said body and said buttress are defined in said backing member;

said second body surface of said body is defined in said bearing insert member; and said securing step includes the steps of (i) securing said backing member to the glenoid surface of the scapula such that (a) said first body surface of said backing member is positioned in contact with the glenoid surface of the scapula, and (b) said portion of said buttress of said backing member is positioned in said buttress-shaped recess; and (ii) securing said bearing insert member to said backing member.

31. The method of claim 28, wherein:

said buttress include a first buttress surface and a second buttress surface; and said first buttress surface is positioned relative to said medial surface at an angle θ wherein 45°<θ<135°.

32. The method of claim 31, wherein said first buttress surface is positioned perpendicular to said second buttress surface.

33. An augmented glenoid component for securement to a glenoid surface of a scapula so as to provide a bearing surface for a head portion of a humerus, the augmented glenoid component comprising:

a body having a medial surface and a humerus surface;

said medial surface configured to contact the glenoid surface of the scapula;

said humerus surface configured to be contacted by the head portion of the humerus;

an interruption extending from said medial surface and defining a first interruption surface positioned relative to said medial surface at an angle θ in which 45°<θ<135°, and a second interruption surface positioned relative to a line parallel to said medial surface at an angle Φ in which 0°<Φ<90°; and anchoring, wherein said anchoring extends from said medial surface, and wherein said anchoring extends entirely from said interruption.

34. An augmented glenoid component for securement to a glenoid surface of a scapula so as to provide a bearing surface for a head portion of a humerus, the augmented glenoid component comprising:

a body having a medial surface and a humerus surface;

said medial surface configured to contact the glenoid surface of the scapula;

said humerus surface configured to be contacted by the head portion of the humerus;

an interruption extending from said medial surface and defining a first interruption surface positioned relative to said medial surface at an angle θ in which 45°<θ<135°, and a second interruption surface positioned relative to a line parallel to said medial surface at an angle Φ in which 0°<Φ<90°; and anchoring, wherein said body comprises a backing member having said medial surface, said humerus body surface, and said interruption defined therein; and the augmented glenoid component further comprises: a bearing insert member securable to said backing member, wherein said backing member includes a plurality of holes each of which is configured to allow passage of a securing member for securing said backing member to the glenoid surface of the scapula, and wherein said plurality of holes extend outwardly from said interruption.

35. An augmented glenoid component for securement to a glenoid surface of a scapula so as to provide a bearing surface for a head portion of a humerus, the augmented glenoid component comprising:

a body having a medial surface and a humerus surface;

said medial surface configured to contact the glenoid surface of the scapula;

said humerus surface configured to be contacted by the head portion of the humerus;

an interruption extending from said medial surface and defining a first interruption surface positioned relative to said medial surface at an angle θ in which 45°<θ<135°, and a second interruption surface positioned relative to a line parallel to said medial surface at an angle Φ in which 0°<Φ<90°; and anchoring, wherein said body comprises a backing member having said medial surface, said humerus body surface, and said interruption defined therein; and the augmented glenoid component further comprises: a bearing insert member securable to said backing member, wherein said backing member includes a plurality of holes each of which is configured to allow passage of a securing member for securing said backing member to the glenoid surface of the scapula, and wherein said plurality of holes extend outwardly from and are distributed in said medial surface and said interruption.

36. A method of securing an augmented glenoid component to a glenoid surface of a scapula so as to provide a bearing surface for a head portion of a humerus, said augmented glenoid component having (i) a body having (a) a first body surface configured to contact the glenoid surface of the scapula, and (b) a second body surface configured to be contacted by the head portion of the humerus, and (ii) a buttress extending from said first body surface, the method comprising the steps of:

forming a buttress-shaped recess in a glenoid surface of a scapula; and securing said augmented glenoid component to the glenoid surface of the scapula such that (i) said first body surface is positioned in contact with the glenoid surface of the scapula, and (ii) said buttress is positioned in said step-shaped recess, wherein said augmented glenoid component further has an anchor; and wherein said securing step includes the steps of: (i) forming an anchor hole in the glenoid surface of the scapula, and (ii) advancing said anchor into said anchor hole.

* * * * *